US 9,395,308 B2

United States Patent
Yun

(10) Patent No.: US 9,395,308 B2
(45) Date of Patent: Jul. 19, 2016

(54) APPARATUS FOR QUANTITATIVE MEASUREMENTS OF STRESS DISTRIBUTIONS FROM MECHANOLUMINESCENE MATERIALS

(71) Applicant: Gunjin Yun, Copley, OH (US)

(72) Inventor: Gunjin Yun, Copley, OH (US)

(73) Assignee: University of Akron, Akron, OH (US)

( * ) Notice: Subject to any disclaimer, the term of this patent is extended or adjusted under 35 U.S.C. 154(b) by 132 days.

(21) Appl. No.: 14/511,373

(22) Filed: Oct. 10, 2014

(65) Prior Publication Data

US 2015/0103333 A1  Apr. 16, 2015

Related U.S. Application Data

(60) Provisional application No. 61/889,090, filed on Oct. 10, 2013.

(51) Int. Cl.
  *G01B 11/16* (2006.01)
  *G01N 21/88* (2006.01)
  *G01L 1/24* (2006.01)

(52) U.S. Cl.
  CPC .............. *G01N 21/8803* (2013.01); *G01L 1/24* (2013.01); *G01N 2201/061* (2013.01)

(58) Field of Classification Search
  CPC .............. G01N 1/405; G01N 33/5308; G01N 2001/4088; G01N 21/4795; G01N 2333/35; G01N 2800/52; G01N 2800/56; G01N 33/54353; G01N 33/551; G01N 33/56911; G01N 33/56916; G01N 33/6845; G01N 11/16
  See application file for complete search history.

(56) References Cited

U.S. PATENT DOCUMENTS

| | | | | |
|---|---|---|---|---|
| 2001/0017059 A1* | 8/2001 | Xu | ............................. | G01L 1/24 73/800 |
| 2003/0016351 A1* | 1/2003 | Gomelskiy | ............ | G01N 21/70 356/311 |
| 2007/0186674 A1* | 8/2007 | Hyodo | ................... | G01N 3/068 73/826 |
| 2008/0120045 A1* | 5/2008 | Hyodo | ....................... | G01L 1/24 702/42 |
| 2009/0170214 A1* | 7/2009 | Meek | .................... | G01N 21/645 436/172 |
| 2009/0286076 A1* | 11/2009 | Xu | ............................ | C09D 5/22 428/339 |
| 2009/0310121 A1* | 12/2009 | Lam | ..................... | G01B 11/168 356/35 |
| 2015/0103333 A1* | 4/2015 | Yun | ..................... | G01N 21/8803 356/32 |
| 2015/0241363 A1* | 8/2015 | Tuch | .................... | A61B 5/0077 250/362 |

\* cited by examiner

*Primary Examiner* — Michael P Stafira
(74) *Attorney, Agent, or Firm* — Renner Kenner Greive Bobak Taylor & Weber

(57) ABSTRACT

An apparatus for measuring mechanoluminescent light includes a chamber defining an enclosure for a portion of a structure to be monitored and providing an opening fitted onto the structure. The structure has a mechanoluminescent material thereon. The apparatus further includes an imaging sensor positioned and configured to take images of the mechanoluminescent material and an electronic controller in wired or wireless communication with the imaging sensor, the electronic controller being capable of controlling the properties of the imaging sensor and processing the images of the mechanoluminescent material.

14 Claims, 1 Drawing Sheet

APPARATUS FOR QUANTITATIVE MEASUREMENTS OF STRESS DISTRIBUTIONS FROM MECHANOLUMINESCENE MATERIALS

CROSS-REFERENCE TO RELATED APPLICATION

This application claims priority to U.S. Provisional Patent Application No. 61/889,090 filed on Oct. 10, 2013, the contents of which are incorporated herein by reference.

FIELD OF THE INVENTION

The present invention generally relates to an apparatus for measuring the mechanoluminescence of a mechanoluminescent material. The present invention further relates to an apparatus that measures the quantitative stress or strain distributions of a mechanoluminescent material using mechanoluminescence light intensity. The present invention further relates to an apparatus having a mechanoluminescent material within a chamber, where the apparatus photoexcites the mechanoluminescent material, takes images of the mechanoluminescent material, and monitors environmental conditions within the chamber.

BACKGROUND OF THE INVENTION

It is previously known to use mechanoluminescence (ML) materials for the visualization of stress or crack distributions through the use of mechanically-induced light emission. These ML materials can be applied to a structure for monitoring the health of the structure. Monitoring is performed by sensors capable of measuring deformations of and stresses on the structures. Such known sensors can utilize strain gauges, photoelasticity, and digital image correlation for measuring the stress experienced by a structure. A goal of these sensors is the diagnosis of impending structural failure, which can lead to the subsequent correction of the structural failure mechanisms.

Existing applications of using sensors for monitoring ML materials are limited. For instance, strain gauges are generally limited to point-by-point measurements. Also, existing sensors are generally not capable of revealing full field visualization of stresses.

Thus, there is a need in the art for an improved apparatus for measuring the mechanoluminescence of a mechanoluminescent material. There is also a need in the art for an apparatus for measuring the quantitative stress or strain distributions of a mechanoluminescent material using mechanoluminescence light intensity.

SUMMARY OF THE INVENTION

In a first embodiment, the present invention provides an apparatus for measuring mechanoluminescent light comprising a chamber defining an enclosure for a portion of a structure to be monitored and providing an opening fitted onto the structure, the structure having a mechanoluminescent material thereon, an imaging sensor positioned and configured to take images of the mechanoluminescent material, and an electronic controller in wired or wireless communication with the imaging sensor, the electronic controller being capable of controlling the properties of the imaging sensor and processing the images of the mechanoluminescent material.

In a second embodiment, the present invention provides an apparatus as in the first embodiment, the chamber having a side positioned opposite of the structure, wherein the side positioned opposite of the structure includes the imaging sensor positioned therein.

In a third embodiment, the present invention provides an apparatus as in either the first or second embodiment, wherein the imaging sensor is positioned entirely inside the enclosure of chamber.

In a fourth embodiment, the present invention provides an apparatus as in any of the first through third embodiments, wherein the image processing reveals stress distribution or crack visualization of the structure.

In a fifth embodiment, the present invention provides an apparatus as in any of the first through fourth embodiments, further comprising a thermocouple for monitoring temperature in order to compensate the processing of the images of the mechanoluminescent material.

In a sixth embodiment, the present invention provides an apparatus as in any of the first through fifth embodiments, wherein the chamber is constructed from black fiber cotton and steel wire frames.

In a seventh embodiment, the present invention provides an apparatus as in any of the first through sixth embodiments, wherein the chamber is constructed from black acrylic plates.

In an eighth embodiment, the present invention provides an apparatus as in any of the first through seventh embodiments, wherein the chamber blocks a substantial amount of external light from entering the enclosure of the chamber.

In a ninth embodiment, the present invention provides an apparatus as in any of the first through eighth embodiments, wherein the chamber is sealed onto the surface and blocks all external light from entering the enclosure of the chamber.

In a tenth embodiment, the present invention provides an apparatus as in any of the first through ninth embodiments, wherein the imaging sensor is selected from the group consisting of charge-coupled device cameras, active-pixel sensor cameras, and complementary metal-oxide-semiconductor cameras.

In an eleventh embodiment, the present invention provides an apparatus as in any of the first through tenth embodiments, further comprising a light source to photoexcite the mechanoluminescent material on the structure.

In a twelfth embodiment, the present invention provides an apparatus as in any of the first through eleventh embodiments, wherein the light source is selected from light-emitting diode lights, incandescent lights, fluorescent lights, and neon lights.

In a thirteenth embodiment, the present invention provides a method of using an apparatus for measuring mechanoluminescent light comprising the steps of providing a structure having mechanoluminescent material thereon; providing a chamber having an imaging sensor, where the chamber defines an enclosure for the portion of the structure to be monitored and provides an opening fitted onto the structure; photoexciting the mechanoluminescent material; allowing the mechanoluminescent material to produce mechanoluminescence light; and capturing images of the mechanoluminescence light.

In a fourteenth embodiment, the present invention provides a method as in the thirteenth embodiment, further comprising the steps of processing the images of mechanoluminescence light from a mechanoluminescent material and using the processed images to determine stress distribution or crack visualization of the structure.

BRIEF DESCRIPTION OF THE DRAWINGS

Advantages of the present invention will become better understood with regard to the following description, appended claims, and accompanying drawings wherein:

DETAILED DESCRIPTION OF ILLUSTRATIVE EMBODIMENTS

Figure 1:
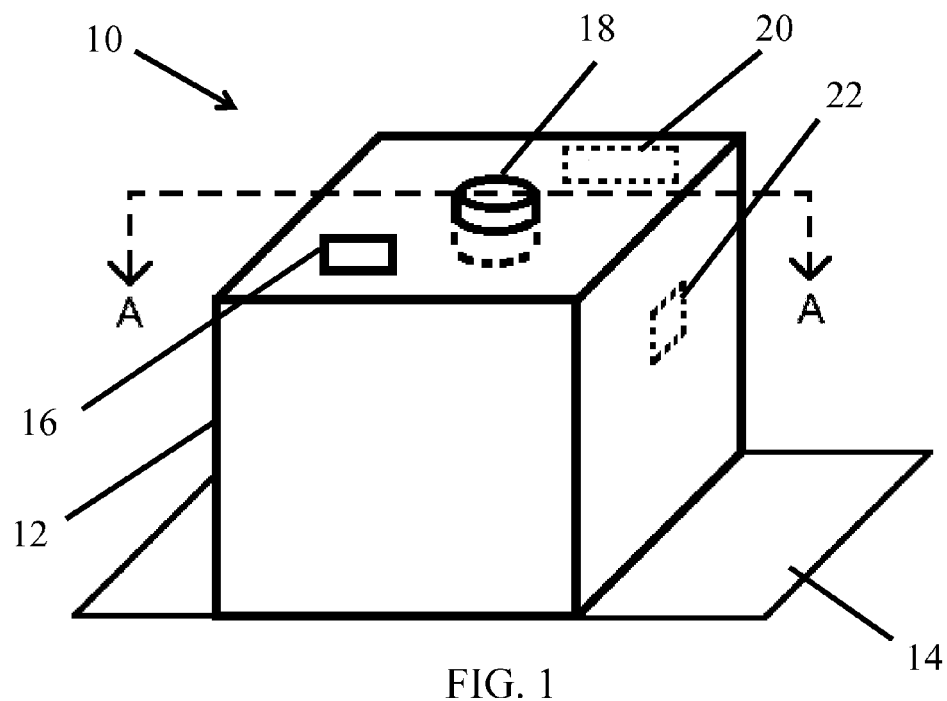
FIG. 1 is a schematic representation of one or more embodiments of the present invention.
Figure 2:
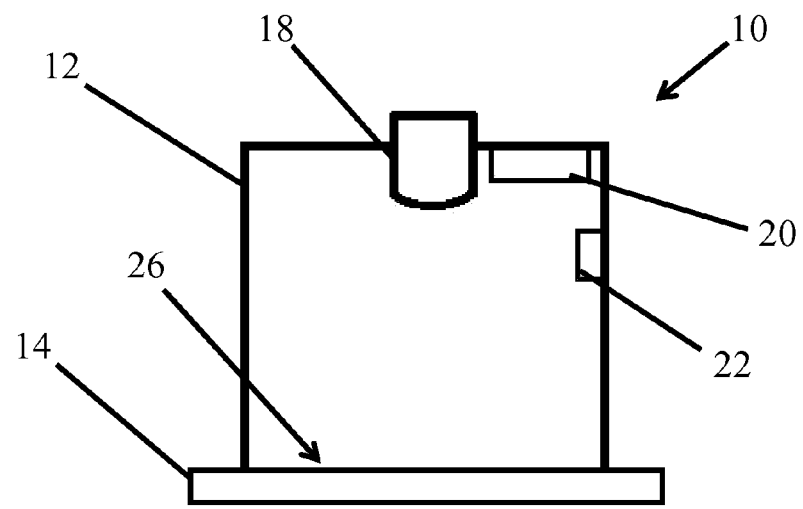
FIG. 2 is a schematic representation of the cross-sectional view at line A-A of FIG. 1.

An apparatus, generally indicated by the numeral 10, of the present invention includes chamber 12 that is capable of measuring the mechanoluminescence of a structure 14 having a mechanoluminescent material thereon. Chamber 12 measures the quantitative stress or strain distributions of a mechanoluminescent material by analyzing the intensity of mechanoluminescence light.

Chamber 12 can include various components for performing various roles. Chamber 12 comprises one or more of the following: an electronic controller 16, an imaging sensor 18, a light source 20, and a thermocouple 22. In one or more embodiments, an apparatus 10 consists of a chamber 12 consisting of an electronic controller 16, an imaging sensor 18, a light source 20, and a thermocouple 22. In one or more embodiments, an apparatus 10 comprises a chamber 12 comprising an electronic controller 16, an imaging sensor 18, a light source 20, and a thermocouple 22.

As shown in the figures, chamber 12 defines an enclosure for the portion of the structure 14 to be monitored, and provides an opening, generally indicated by the numeral 26, fitted onto the structure so that opening 26 is located on the mechanoluminescent material and any mechanoluminescence light therefrom can be observed by the imaging sensor 18. It should be appreciated a chamber can have any shape so long as the chamber includes an opening such that mechanoluminescence can be observed.

The chamber 12 should be constructed such that it can effectively block light from entering the enclosure of the chamber 12 when the chamber 12 is positioned on a structure 14. The enclosure should be blocked from outside light so that the full mechanoluminescence light can be fully observed. In one or more embodiments, the chamber 12 is sealed onto the surface in order to block any external light.

It is preferred that chamber 12 is made from a light weight material that is effective at blocking any external light in order to secure a dark space in the enclosure. Examples of suitable materials include metals, dark color plastics, such as black acrylic plates, and dark color fibers with a support material, such as black fiber cotton with wire frames. Composites of fiber mats with matrix materials supporting them (such as fiberglass and epoxy) are also suitable. The chamber 12 can be any size as long as it can be located on structure 14.

Chamber 12 includes an electronic controller 16 for controlling the settings of an imaging sensor 18 and a light source 20. With respect to imaging sensor 18, electronic controller 16 can control when an image is taken, how many images are taken, frame rate, exposure time, gain level, and other camera properties. With respect to light source 20, electronic controller 16 can control whether the light source 20 is illuminated, the duration of illumination, and other properties of the light source. The control or configuration of the imaging sensor 18 and light source 20 can be done through an application programming interface (API).

Electronic controller 16 can also include the ability to monitor a thermocouple 22, as by reading data from the thermocouple 22. Such monitoring could occur by electronic controller 16 displaying the data from the thermocouple 22 on an electronic screen or other display device included as part of the electronic controller 16.

As shown in the figures, electronic controller 16 can be positioned on a top side of chamber 12. In other embodiments, electronic controller 16 can be positioned on the left, right, front, or rear sides of chamber 12. In other embodiments, electronic controller 16 is positioned away from chamber 12. In one or more embodiments, electronic controller 16 is a computer.

Where an electronic controller 16 receives images from imaging sensor 18, controls one or more other components, or monitors one or more other components, the electronic controller 16 is capable of communicating with the components as known to those of ordinary skill in the art. Such communication can occur by wired communications or wireless communications.

Electronic controller 16 uses previously developed correlations in order to use the images, and the associated mechanoluminescence data therein, and the temperature data to read the amount of stress or strain based on the mechanoluminescence. Such correlations can be developed through the use of control graphs or distribution graphs. Such correlations can also be produced through software or other computer programming. These correlations, and the measured data, allow the electronic controller 16 to determine stress or strain on structures over a predetermined time.

In one or more embodiments, imaging sensor 18 is positioned in an opening in one side of chamber 12. As shown in figures, it is preferred that imaging sensor 18 is positioned in the side directly opposite opening 26. In other embodiments, a camera is positioned in the left, right, front, or rear sides of chamber 12 and is at an angle or manipulated in order to be capable of observing a structure 14. In other embodiments, the imaging sensor 18 is positioned entirely inside the enclosure of chamber 12.

Imaging sensor 18 is positioned and configured to take images of the structure 14. The images capture the mechanoluminescence of the mechanoluminescent material. The images are then be processed in order to reveal dynamic changes in light intensity from the ML material 14. In one or more embodiments, electronic controller 16 is used for the image processing. An example of image processing is Vision Builder AI software from National Instruments.

Imaging sensor 18 is selected from the group consisting of charge-coupled device (CCD) cameras, active-pixel sensor (APS) cameras, and complementary metal-oxide-semiconductor (CMOS) cameras. Images can be obtained at a fixed frame per second with a consistent gain level setting.

The light source 20 is provided to photoexcite the mechanoluminescent material on the structure 14. Photoexcitation is the photoelectrochemical process of electron excitation by photon absorption, when the energy of the photon is too low to cause photoionization. The absorption of the photon takes place in accordance with Planck's quantum theory. A mechanoluminescent material must be photoexcited before it will give any mechanoluminescence effect. In one or more embodiments, the mechanoluminescent material is fully photoexcited. The light source 20 can be selected from light-emitting diode (LED) lights, incandescent lights, fluorescent lights, and neon lights. In one or more embodiments, the photoexcitation wavelength of the ML material is in the range of from 200 nm or more to 470 nm or less.

Thermocouple 22 can be provided to monitor the environmental conditions, specifically the temperature, within the chamber 12. A thermocouple is a temperature-measuring device consisting of two dissimilar conductors that contact each other at one or more locations. It produces a voltage when the temperature of one of the locations differs from the reference temperature at other parts of the circuit. Thermocouples can be used sensor for both measurement and for controlling the temperature with the chamber 12.

Thermocouple 22 can be selected from the group consisting of nickel alloy thermocouples, platinum/rhodium alloy thermocouples, tungsten/rhenium alloy thermocouples, gold/iron alloy thermocouples, noble metal alloys, platinum/molybdenum alloy thermocouples, iridium/rhodium alloy thermocouples, and pure noble metal thermocouples.

Apparatus 10 can use thermocouple 22 for monitoring temperature in order to compensate the ML measurements. Collected ML data is temperature sensitive so temperature data is needed for compensation of the measurements.

The structure 14 can be any substrate having mechanoluminescent material thereon. Mechanoluminescence is light emission resulting from any mechanical action on a solid. Compositions comprising ML material can be used as sensing materials that emit light in response to mechanical stress and deformation.

In one or more embodiments, the structure and mechanoluminescent material can be selected from those structures and mechanoluminescent materials disclosed in co-pending International Application PCT/US2014/054925, which is incorporated herein by reference. For example, the structure can be a curved structure having a paintable medium thereon and the mechanoluminescent material can be ML particles selected from the group consisting of ZnS:Mn; $SrAl_2O_4$:Eu (SAOE); $SrAl_2O_4$:Eu,Dy (SAOED); $SrAl_2O_4$:Ce; $SrAl_2O_4$:Ce,Ho; $SrMgAl_6O_{11}$:Eu; $SrCaMgSi_2O_7$:Eu; $Sr_2MgSi_2O_7$:Eu; $Ca_2MgSi_2O_7$:Eu,Dy; $CaYAl_3O_7$:Eu; $Ca_2Al_2SiO_7$:Ce; and combinations thereof.

Embodiments of the present invention include one or more methods of using the apparatus describe above. A method of using the apparatus can include one or more of the following steps: providing a structure having mechanoluminescent material thereon; providing a chamber having an imaging sensor, where the chamber defines an enclosure for the portion of the structure to be monitored and provides an opening fitted onto the structure; photoexciting a mechanoluminescent material; allowing a mechanoluminescent material to produce mechanoluminescence light; capturing images of mechanoluminescence light from a mechanoluminescent material; processing images of mechanoluminescence light from a mechanoluminescent material; and using the processed images to determine stress distribution or crack visualization of the structure. Methods of the present invention can further include utilizing the apparatus at predetermined intervals to monitor stress distribution or crack visualization of a structure at the predetermined intervals. Such predetermined intervals can be further established as a method for routine monitoring of the structure.

The present invention offers one or more of the following advantages: an improved apparatus for measuring mechanoluminescence, quantitative measurement of stress distributions, quantitative measurement of stress distributions of crack damage, crack damage visualization, and stress distribution visualization.

In light of the foregoing, it should be appreciated that the present invention significantly advances the art by providing an improved apparatus for measuring the mechanoluminescence of a mechanoluminescent material and associated methods of use. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. An apparatus for measuring mechanoluminescent light comprising
    a chamber defining an enclosure for a portion of a structure to be monitored and providing an opening fitted onto the structure, the structure having a mechanoluminescent material thereon,
    an imaging sensor positioned and configured to take images of the mechanoluminescent material, and
    an electronic controller in wired or wireless communication with the imaging sensor, the electronic controller being capable of controlling the properties of the imaging sensor and processing the images of the mechanoluminescent material.

2. The apparatus of claim 1, the chamber having a side positioned opposite of the structure, wherein the side positioned opposite of the structure includes the imaging sensor positioned therein.

3. The apparatus of claim 1, wherein the imaging sensor is positioned entirely inside the enclosure of chamber.

4. The apparatus of claim 1, wherein the image processing reveals stress distribution or crack visualization of the structure.

5. The apparatus of claim 1, further comprising a thermocouple for monitoring temperature in order to compensate the processing of the images of the mechanoluminescent material.

6. The apparatus of claim 1, wherein the chamber is constructed from black fiber cotton and steel wire frames.

7. The apparatus of claim 1, wherein the chamber is constructed from black acrylic plates.

8. The apparatus of claim 1, wherein the chamber blocks a substantial amount of external light from entering the enclosure of the chamber.

9. The apparatus of claim 1, wherein the chamber is sealed onto the surface and blocks all external light from entering the enclosure of the chamber.

10. The apparatus of claim 1, wherein the imaging sensor is selected from the group consisting of charge-coupled device cameras, active-pixel sensor cameras, and complementary metal-oxide-semiconductor cameras.

11. The apparatus of claim 1, further comprising a light source to photoexcite the mechanoluminescent material on the structure.

12. The apparatus of claim 1, wherein the light source is selected from light-emitting diode lights, incandescent lights, fluorescent lights, and neon lights.

13. A method of using an apparatus for measuring mechanoluminescent light comprising the steps of
    providing a structure having mechanoluminescent material thereon;
    providing a chamber having an imaging sensor, where the chamber defines an enclosure for the portion of the structure to be monitored and provides an opening fitted onto the structure;
    photoexciting the mechanoluminescent material;
    allowing the mechanoluminescent material to produce mechanoluminescence light; and
    capturing images of the mechanoluminescence light.

14. The method of claim 13, further comprising the steps of
    processing the images of mechanoluminescence light from a mechanoluminescent material; and
    using the processed images to determine stress distribution or crack visualization of the structure.

* * * * *